US011104945B2

(12) United States Patent
Wang et al.

(10) Patent No.: US 11,104,945 B2
(45) Date of Patent: *Aug. 31, 2021

(54) SELECTIVE AMPLIFICATION OF OVERLAPPING AMPLICONS

(71) Applicant: Pillar Biosciences Inc., Natick, MA (US)

(72) Inventors: Zhaohui Wang, Southborough, MA (US); Gang Song, Newton, MA (US)

(73) Assignee: Pillar Biosciences Inc., Natick, MA (US)

( * ) Notice: Subject to any disclaimer, the term of this patent is extended or adjusted under 35 U.S.C. 154(b) by 229 days.

This patent is subject to a terminal disclaimer.

(21) Appl. No.: 16/290,736

(22) Filed: Mar. 1, 2019

(65) Prior Publication Data

US 2019/0256892 A1 Aug. 22, 2019

Related U.S. Application Data

(63) Continuation of application No. 15/396,132, filed on Dec. 30, 2016, now Pat. No. 10,221,448, which is a continuation-in-part of application No. 15/057,343, filed on Mar. 1, 2016, now Pat. No. 10,011,869.

(60) Provisional application No. 62/129,360, filed on Mar. 6, 2015.

(51) Int. Cl.
*C12Q 1/68* (2018.01)
*C12Q 1/686* (2018.01)

(52) U.S. Cl.
CPC .................... *C12Q 1/686* (2013.01)

(58) Field of Classification Search
CPC .............. C12Q 1/686; C12Q 2525/161; C12Q 2527/107; C12Q 2537/143
See application file for complete search history.

(56) References Cited

U.S. PATENT DOCUMENTS

| 6,287,825 | B1 | 9/2001 | Weissman et al. |
| 8,318,434 | B2 | 11/2012 | Cuppens |
| 10,011,869 | B2 | 7/2018 | Wang et al. |
| 10,221,448 | B2 | 3/2019 | Wang et al. |
| 10,316,359 | B2 | 6/2019 | Makarov et al. |
| 2009/0291475 | A1 | 11/2009 | Lao et al. |
| 2010/0129874 | A1 | 5/2010 | Mitra et al. |
| 2010/0227329 | A1 | 9/2010 | Cuppens |
| 2010/0285537 | A1 | 11/2010 | Zimmermann |
| 2013/0005585 | A1 | 1/2013 | Anderson et al. |
| 2014/0200146 | A1 | 7/2014 | Xie et al. |

FOREIGN PATENT DOCUMENTS

| EP | 0519338 | A1 | 12/1992 |
| WO | 9746704 | A1 | 12/1997 |
| WO | 9808970 | A1 | 3/1998 |
| WO | 2004/016811 | A2 | 2/2004 |
| WO | 2007018601 | A1 | 2/2007 |
| WO | 2007052006 | A1 | 5/2007 |
| WO | 2007087291 | A2 | 8/2007 |
| WO | 2008/033442 | A2 | 3/2008 |
| WO | 2009133466 | A2 | 11/2009 |
| WO | 2012012037 | A1 | 1/2012 |
| WO | 2013081755 | A1 | 6/2013 |
| WO | 2013081864 | A1 | 6/2013 |
| WO | 2013181170 | A1 | 12/2013 |
| WO | 2015/026873 | A1 | 2/2015 |
| WO | 2015120177 | A1 | 8/2015 |
| WO | 2015134552 | A1 | 9/2015 |
| WO | 2016037389 | A1 | 3/2016 |

OTHER PUBLICATIONS

International Search Report dated May 17, 2016 in PCT/US2016/020284.
Mamanova, et al., "Target-enrichment strategies for next-generation sequencing", Nature Methods, vol. 7, No. 2, Feb. 2010, pp. 111-118.
Mertes, et al., "Targeted enrichment of genomic DNA regions for next-generation sequencing", Briefings in Functional Genomics, Downloaded from http://bfgp.oxfordjournals.org/by guest on Jan. 27, 2015, pp. 1-13.
Wen, et al., "Universal Multiplex PCR: a novel method of simultaneous amplification of multiple DNA fragments", Plant Methods, vol. 8:32, Aug. 2012, pp. 1-9.
European Search Report dated Dec. 7, 2017 in EP Patent Application No. 16762140.8.
"Bio Watch PCR Assays: Building Confidence, Ensuring Reliability: Abbreviated Version", National Research Council & Institute of Medicine, The National Academies Press (2015), 2005.
"Improved methods for processing DNA substrates", U.S. Appl. No. 61/934,515, filed Jan. 31, 2014.
Brownie, Jannine , et al., "The elimination of primer-dimer accumulation in PCR", Nucleic Acids Res. 25(16), 3235-3241 (1997).
Chamberlain, Jeffrey S, et al., "Deletion screening of the Duchenne muscular dystrophy locus via multiplex DNA amplification", Nucleic Acids Res. 16(23):11141-56 (1988), 1988.

(Continued)

*Primary Examiner* — David C Thomas
(74) *Attorney, Agent, or Firm* — Perkins Coie LLP; Viola T. Kung

(57) ABSTRACT

The present invention relates to a scalable multiplex PCR method that can simultaneously amplify overlapping amplicons without the drawbacks of conventional multiplex PCR. The method selectively amplifying target nucleic acid fragments having an overlapping region. The method comprises the steps of: obtaining a first nucleic acid sequence comprising a first tag t2 and a first forward primer F1, obtaining a second nucleic acid sequence comprising a second tag t1 and a first reverse primer R1, obtaining a third nucleic acid sequence comprising the second tag t1 and a second forward primer F2, obtaining a fourth nucleic acid sequence comprising a third tag t3 and a second reverse primer R2, wherein each primer is a gene-specific primer; performing initial cycles of PCR; and then performing later cycles of PCR at higher annealing temperatures to obtain amplification products.

16 Claims, 7 Drawing Sheets

Specification includes a Sequence Listing.

(56) References Cited

OTHER PUBLICATIONS

Edwards, Mary C, et al., "Multiplex PCR: Advantages, Development, and Applications", PCR Methods Appl. 3, 1994, S65-S75.
Fowler, Samantha, et al., "Concepts of Biology", OpenStax (2013, as reprint in 2014, 2017), https://openstax.org/details/books/concepts-biology.
Gardner, Shea N, et al., "Multiplex Degenerate Primer Design for Targeted Whole Genome Amplification of Many Viral Genomes", Adv Bioinformatics. 2014(101894):1-8, 2014.
Gardner, Shea N, "Supplementary Information", Jan. 7, 2021.
Garibyan, Lilit, et al., "Research Techniques Made Simple: Polymerase Chain Reaction (PCR)", J Invest Dermatol. 133(3):e6 (2013).
Henegariu, O, et al., "Multiplex PCR: Critical Parameters and Step-by-Step Protocol", Biotechniques. 23(3):, 504-511 (1997).
Kwok, Shirley, et al., "A Guide to the Design and Use of Mismatched and Degenerate Primers", PCR Methods Appl. 3, S39-S47 (1994).
Lorenz, Todd C, "Polymerase Chain Reaction: Basic Protocol Plus Troubleshooting and Optimization Strategies", J Vis Exp. (63):e3998 (2012).
Markoulatos, P., et al., "Multiplex Polymerase Chain Reaction: A Practical Approach", J Clin Lab Anal. 16:47-51 (2002).
Telenius, Håkan, et al., "Degenerate Oligonucleotide-Primed PCR: General Amplification of Target DNA by a Single Degenerate Primer", Genomics 13:718-725 (1992).
Yang, Xiaohan, et al., "Recent developments in primer design for DNA polymorphism and mRNA profiling in higher plants", Plant Methods 2:4, (2006).
Zong, Chenghang, et al., "Genome-Wide Detection of Single-Nucleotide and Copy-Number Variations of a Single Human Cell", Science 338(6114):1622-1626 (2012).

SEQUENCE LISTING

<160> NUMBER OF SEQ ID NOS: 27

<210> SEQ ID NO 1
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 1
gtgaaagaca tatttacaga cagtttc                                        27

<210> SEQ ID NO 2
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 2
cttgtgagct ggtctgaatg t                                              21

<210> SEQ ID NO 3
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 3
agggaagctt cataagtcag tc                                             22

<210> SEQ ID NO 4
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 4
tcctctaaca ctcccttaac tttgt                                          25

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
caacgatcgt cgaaattcgc                                                20

<210> SEQ ID NO 6
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 6
tacacgacgc tcttccgatc t                                              21

<210> SEQ ID NO 7
<211> LENGTH: 47
<212> TYPE: DNA
<213> ORGANISM: Artificial Sequence

```
<220> FEATURE:
<223> OTHER INFORMATION: synthetic oligonucleotide

<400> SEQUENCE: 7
caacgatcgt cgaaattcgc gtgaaagaca tatttacaga cagtttc          47

<210> SEQ ID NO 8
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 8
tacacgacgc tcttccgatc tgtgaaagac atatttacag acagtttc          48

<210> SEQ ID NO 9
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 9
tacacgacgc tcttccgatc tcttgtgagc tggtctgaat gt          42

<210> SEQ ID NO 10
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 10
caacgatcgt cgaaattcgc cttgtgagct ggtctgaatg t          41

<210> SEQ ID NO 11
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 11
caacgatcgt cgaaattcgc agggcttgtg agctggtctg aatgt          45

<210> SEQ ID NO 12
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 12
caacgatcgt cgaaattcgc agggaagcct tgtgagctgg tctgaatgt          49

<210> SEQ ID NO 13
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 13
caacgatcgt cgaaattcgc agggaagctt cacttgtgag ctggtctgaa tgt          53
```

```
<210> SEQ ID NO 14
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 14
caacgatcgt cgaaattcgc agggaagctt cataag                                 36

<210> SEQ ID NO 15
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 15
caacgatcgt cgaaattcgc agggaagctt cataagtcag tc                          42

<210> SEQ ID NO 16
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 16
tacacgacgc tcttccgatc ttcctctaac actcccttaa ctttgt                      46

<210> SEQ ID NO 17
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 17
caacgatcgt cgaaattcgc actgtgtgta atatttgcgt gctt                        44

<210> SEQ ID NO 18
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 18
tacacgacgc tcttccgatc tttctctttt tgcagttctt ttggt                       45

<210> SEQ ID NO 19
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 19
caacgatcgt cgaaattcgc cttcaaagtc ttgtaaaggg gaga                        44

<210> SEQ ID NO 20
<211> LENGTH: 43
<212> TYPE: DNA
<213> ORGANISM: Artificial Sequence
<220> FEATURE:
<223> OTHER INFORMATION: synthetic oligonucleotide
```

```
<400> SEQUENCE: 20
tacacgacgc tcttccgatc tttgaaccag acaaaagagc ttg        43

<210> SEQ ID NO 21
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 21
caacgatcgt cgaaattcgc gaaatttctc ttttggaaag taattca     47

<210> SEQ ID NO 22
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 22
tacacgacgc tcttccgatc ttgtggtttg aaattatatt ccagtctt    48

<210> SEQ ID NO 23
<211> LENGTH: 55
<212> TYPE: DNA
<213> ORGANISM: Artificial Sequence
<220> FEATURE:
<223> OTHER INFORMATION: synthetic oligonucleotide

<400> SEQUENCE: 23
tacacgacgc tcttccgatc tcttcaaagt cttctctttt tgcagttctt ttggt    55

<210> SEQ ID NO 24
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 24
tacacgacgc tcttccgatc tcttcaaagt cttgtaaagg ggaga    45

<210> SEQ ID NO 25
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 25
caacgatcgt cgaaattcgc gaaatttctc tttgaaccag acaaaagagc ttg    53

<210> SEQ ID NO 26
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 26
caacgatcgt cgaaattcgc cttgtgagag ggaagcttca taagtcagtc    50

<210> SEQ ID NO 27
```

```
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 27
caacgatcgt cgaaattcgc cttgtgagct ggagggaagc ttcataagtc agtc            54
```

SELECTIVE AMPLIFICATION OF OVERLAPPING AMPLICONS

This application is continuation of U.S. application Ser. No. 15/396,132, filed Dec. 30, 2016; which is continuation-in-part of U.S. application Ser. No. 15/057,343, filed Mar. 1, 2016; which claims priority to U.S. Provisional Application No. 62/129,360, filed Mar. 6, 2015; the content of which is incorporated herein by reference in its entirety.

TECHNICAL FIELD

This invention relates to a method for selectively amplifying target nucleic acid fragments having an overlapping region. The present method enriches copies of target amplicons over copies of the overlapping regions of amplicons.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Dec. 21, 2016, and a size of 5.53 kilobytes. The Sequence Listing filed via EFS-Web is part of the specification and is hereby incorporated in its entirety by reference herein.

BACKGROUND OF THE INVENTION

Multiplex-PCR consists of multiple primer sets within a single PCR mixture to produce amplicons that are specific to different DNA sequences. By targeting multiple genes at once, additional information may be gained from a single test run that would otherwise require several times of the reagents and more time to perform. Annealing temperature for each of the primer sets must be optimized to work correctly within a single reaction. Commercial kits for multiplexing PCR general reagents are available. The technique of multiplex PCR has been used for target enrichment for next-generation sequencing (NGS), which refers to high throughput parallel DNA sequencing technologies. Millions or billions of DNA strands can be sequenced concurrently, yielding substantially high throughput.

One major reason for amplicon drop-out is preferential amplification of the short overlapping regions between two overlapping amplicons during amplification. Currently, to amplify two overlapping DNA amplicons, the primer pairs specifically targeting each amplicon are physically separated into different reaction wells, tubes or micro-droplets. For example, BRCA1 and BRCA2 genes contain large exons that require PCR amplification of overlapping DNA amplicons to ensure 100% base coverage. Ion AmpliSeq BRCA1 and BRCA2 Panel, Qiagen GeneRead Human BRCA1 and BRCA2 Panel, and Multiplicom BRCA MASTR Dx separate primer pairs into 3, 4, 5 primers pools, respectively, primarily due to the inability to amplify overlapping amplicons efficiently. However, multiple primer pools significantly complicate the workflow and increase the cost of testing. RainDance Technologies overcomes this issue by separating PCR primers into thousands of micro-droplets, but on a special expensive instrument.

Combining all PCR primers for two overlapping DNA regions in one multiplex reaction produces four products resulting from four different combinations of the two forward primers with the two different reverse primers. FIG. 1 shows a conventional PCR method. The four PCR products (FIG. 1) are two targeted amplicons (Amplicon 1 and Amplicon 2), one long amplicon (Amplicon 4_long) spanning the entire region of the two targeted amplicons and one short amplicon (Amplicon 3_overlap) containing only the overlapped regions between the two targeted amplicons. Using conventional primer design and PCR conditions, during cycling, the longest amplicon (Amplicon 4_long) serves as DNA template for all four amplicons' amplification, and each of the two targeted amplicons (Amplicon 1 & 2) serves as DNA template for amplification of its own amplicon as well as the shortest amplicon (Amplicon 3_overlap). Assuming that all amplifications occur at 100% efficiency, at PCR cycle n, the amount of the four products— Amplicon 1, Amplicon 2, Amplicon 4_long and Amplicon 3_overlap—will be $n \times 2^n$, $n \times 2^n$, $2^n$, and $n^2 \times 2^n$, respectively. The amount of shortest amplicon (Amplicon 3_overlap) is n times higher than that of each of the two targeted amplicons (Amplicon 1 & 2) which in turn is n times higher than the amount of the longest amplicon (Amplicon 4_long).

DETAILED DESCRIPTION OF THE INVENTION

Definition

An "amplicon" is a piece of DNA or RNA that is the source and/or product of natural or artificial amplification or replication events. In this context, "amplification" refers to the production of one or more copies of a genetic fragment or target sequence, specifically the amplicon. As the product of an amplification reaction, amplicon is used interchangeably with common laboratory terms, such as PCR product.

"Locked nucleic acids" (LNA™) are a class of high-affinity RNA analogues in which the ribose ring is "locked" by a methylene bridge connecting the 2'-O atom and the 4'-C atom resulting in the ideal conformation for Watson-Crick binding. This modification significantly increases the melting temperature of an oligonucleotide and is also very nuclease resistant (www.exiqon.com/lna-technology).

"Peptide nucleic acids" (PNAs) are synthetic homologs of nucleic acids in which the phosphate-sugar polynucleotide backbone is replaced by a flexible pseudo-peptide polymer to which the nucleobases are linked. Because the PNA strand is uncharged, a PNA-DNA duplex will have a higher melting temperature than the corresponding DNA-DNA duplex.

"Universal (PCR) primers" are non-target specific primers that hybridize to universal tags (non-target specific tags such as e.g. t1, t2 and/or t3 in FIG. 2) flanking both ends of any DNA insert sequences. PCR that uses universal primers can amplify any DNA inserts that are flanked by their complementary tag sequences.

The inventors have discovered a scalable multiplex PCR technology, SLIMAMP™ (Stem-Loop Inhibition-Mediated Amplification), which allows for parallel amplification of hundreds of thousands of amplicons in one tube. This novel multiplex PCR method can simultaneously amplify overlapping amplicons without the drawbacks of conventional multiplex PCR, which predominantly amplifies the short overlapping nucleic acid sequences. The present method is a target enrichment method, which enriches copies of target amplicons over copies of the overlapping regions of amplicons.

The present invention is directed to a method for selectively amplifying target nucleic acid fragments having an overlapping region, without a predominant amplification of the short overlapping nucleic acid sequences. The present invention allows all primers in a single primer pool without introducing any additional expensive equipment.

Figure 1:
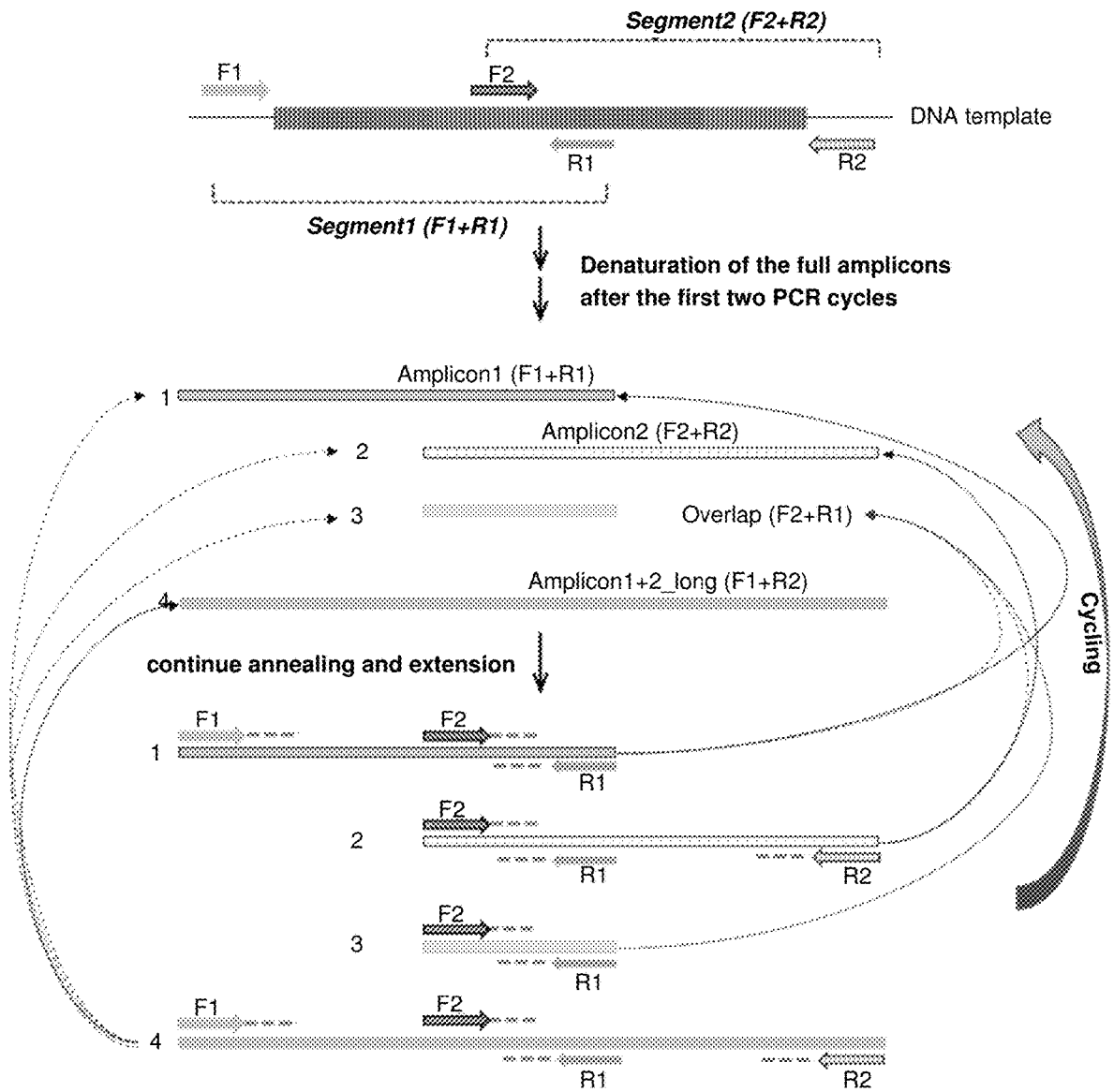
FIG. 1 illustrates a traditional multiplex PCR (prior art), for amplification of overlapping target segments.
Figure 2:
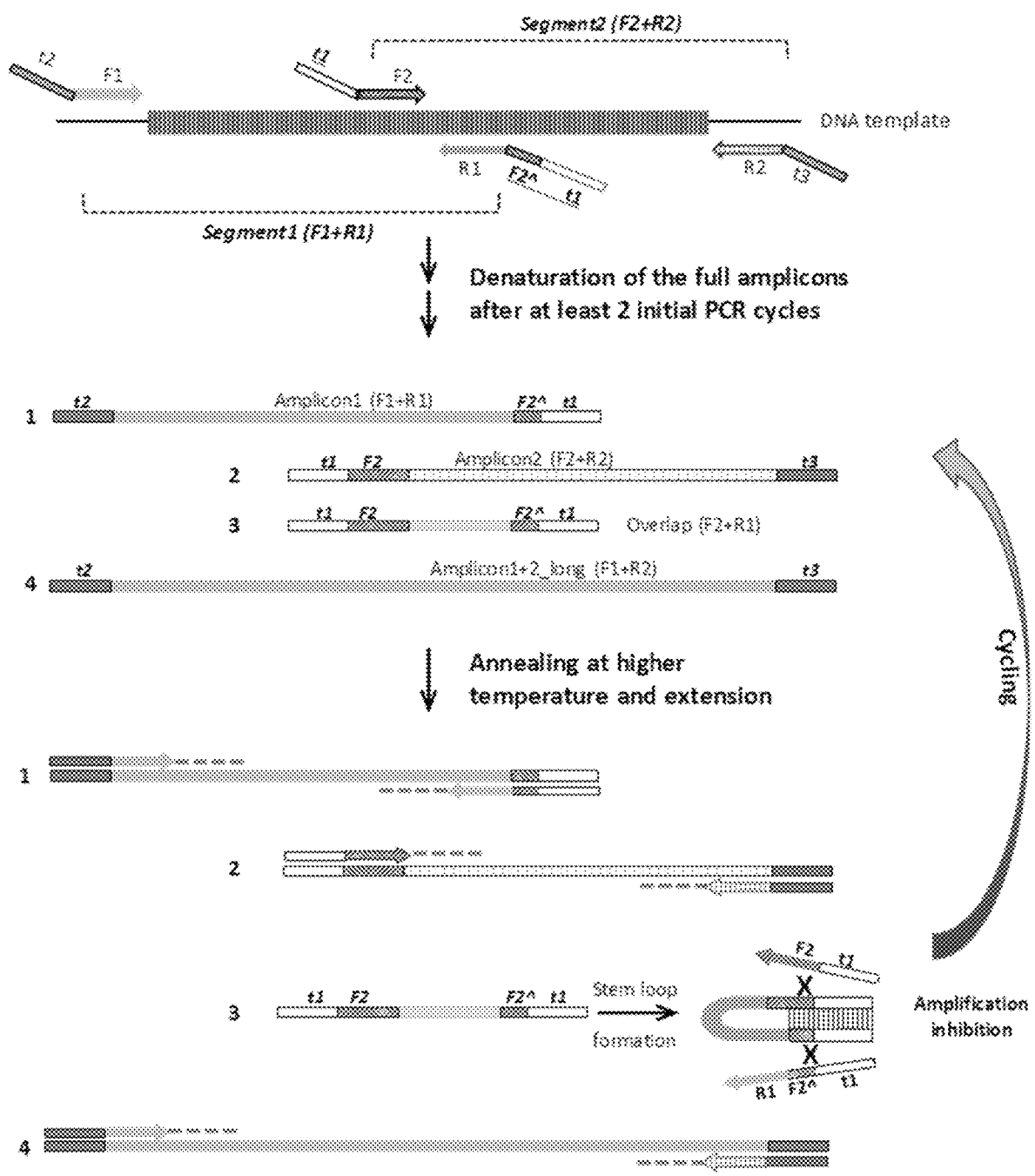
FIG. 2 illustrates one embodiment of a first round of PCR of the present invention, which is the amplification by target-specific primers. F1 and R1 are the forward and reverse primers of target segment 1, while F2 and R2 are the forward and reverse primers of target segment 2. F2^ is a partial sequence of the 5'-end portion of the F2 primer. Tag oligomers of t1, t2 and t3 do not bind to the target. Tags t2 and t3 may share the same sequences and t1 is different. 1, 2, 3 and 4 indicate the amplification products from the combination of four primers. Amplification of Amplicon 3, the short products from F2 and R1, is inhibited by the stem structure that are formed by the two complementary sequences of t1F2^ at the two ends of the same strand of Amplicon 3.

The present invention is illustrated in FIG. 2. FIG. 2 is for illustration purposes and is not meant to limit the invention to the drawings only. The arrangement of tags, forward primers, reverse primers, target nucleic acids, amplicons as described in steps (a)-(d) is shown at the upper part of FIG. 2. The 3'-end of the first target nucleic acid Segment 1 overlaps with the 5'-end of the second target nucleic acid Segment 2.

The present method comprises the steps of: (a) obtaining a first nucleic acid sequence comprising a first tag t2 and a first forward primer F1, (t2F1), complementary to a first target nucleic acid fragment (amplicon 1), (b) obtaining a second nucleic acid sequence comprising a second tag t1 and a first reverse primer R1, (t1R1), complementary to the first target nucleic acid fragment (amplicon 1), (c) obtaining a third nucleic acid sequence comprising the second tag t1 and a second forward primer F2, (t1F2), complementary to a second target nucleic acid fragment (amplicon 2), (d) obtaining a fourth nucleic acid sequence comprising a third tag t3 and a second reverse primer R2, (t3R2), complementary to the second nucleic acid fragment (amplicon 2), wherein the first and the second target nucleic acid fragments have an overlapping region, (e) mixing the first and the second target nucleic acid fragments, the first, the second, the third, and the fourth nucleic acid sequences, and an effective amount of reagents necessary for performing a polymerase chain reaction (PCR); (f) cycling the mixture of (e) through denaturing, annealing and primer extension steps of PCR for at least two times, and (g) cycling the mixture of (f) through denaturing, annealing and primer extension steps of PCR at an annealing temperature higher than that in step (f) to obtain amplification products. The above method steps describe a first round of PCR cycles. The first and the second nucleic acids are designed to amplify Segment 1. The third and the forth nucleic acids are designed to amplify Segment 2.

F1, R1, F2, R2 are gene-specific primers, which are complementary to specific regions of genomic DNA. The length of these primers can be chosen by a person skilled in the art. In general, the gene-specific primers are 6-40, 10-50, 10-40, 10-100, 20-40, or 20-50 nucleotides in length.

Tags t1 and t2 are two different universal tag sequences. Tag t3 can have the same or different sequence as t2. Tag oligomers of t1, t2 and t3 do not bind to the target sequences. Each tag is at the 5' end of each gene-specific primer.

FIG. 2 illustrates one embodiment of the present invention, in which F2^ is a partial sequence of the 5'-end portion of the F2 primer. In other embodiments of the invention, F2^ is replaced with 0 nucleotide (not present) or replaced with F2 (full sequence of F2 primer) in FIG. 2.

In step (f), the mixture of nucleic acids and reagents go through the PCR cycles of denaturing, annealing and primer extension steps at least two times, such as 2-5 times or 2-10 times, at standard PCR temperatures or conditions known to a person skilled in the art. In the very first PCR cycle, amplicons tagged only at one end are generated. In the second PCR cycle, the one-ended tagged amplicons then serve as templates for the other tagged primers to generate 2-ended tagged amplicons. Step (f) is illustrated at the middle part of FIG. 2, wherein Amplicon 1 (F1+R1), Amplicon 2 (F2+R2), Amplicon 4_long (F1+R2), and Amplicon 3_overlap (F2+R1) are generated after the initial cycles. After at least two cycles of PCR, complete amplicons with the tag sequences at both ends are generated and ready for the next round of PCR cycles with an increased annealing temperature of step (g).

In step (g), the mixture of (f) goes through more cycles of PCR of denaturing, annealing and primer extension; this time at an annealing temperature higher than that in step (f), which is an important feature of the present invention. The annealing temperature is increased to prevent the shortest amplicon (Amplicon 3_overlap) to be amplified predominantly.

If the annealing temperature is not increased (as in a conventional PCR method), all amplification follows a conventional way where Amplicons 1, 2, and 4_long can all serve as templates for the amplification of the short amplicon (Amplicon 3_overlap); this is because Amplicons 1, 2, and 4_long all contain the gene-specific parts of the forward and reverse primers of Amplicon 3_overlap. As a result of the amplification (without increasing annealing temperature), the amount of the shortest amplicon (Amplicon 3_overlap) is $n^2 \times 2'$, which is n times higher than that of each of the two targeted amplicons (Amplicons 1 & 2, $n \times 2''$), assuming all amplicons have the same amplification efficiencies. In practice, it is observed that amplification efficiency is affected by amplicon length in which shorter amplicons correlate with higher amplification efficiency (Mallona I, et al, BMC Bioinformatics 2011, 12:404), and therefore, the shorter amplicon amplifies even more favorably.

In step (g) of the present invention, the annealing temperature is increased, and thus a successful primer-template hybridization requires not only the gene-specific parts of the primers, but also the tag parts. When the annealing temperature is increased, Amplicons 1, 2, and 4_long can no longer serve as templates for the amplification of the short amplicon (Amplicon 3_overlap), and only the short amplicon itself (Amplicon 3_overlap) can serve as a template for itself. The present invention features (i) an increasing annealing temperature after the initial at least two PCR cycles, and (ii) a proper arrangement of tags (t1, t2, t3) associated with each amplicon, in particular, F2 and R1 primers are tagged with the same tag t1; such features result in production of $2''$ copies of all amplicons in theory, because each amplicon can only use its own amplicon as a template for its amplification. This is already an improvement over a conventional method, in which Amplicon 3 (short overlap) would yield n times higher than that of target amplicons. In practice, shorter amplicons typically amplify more efficiently than longer amplicons.

In step (g), the annealing temperature is at least 2° C. higher than the annealing temperature in step (f). For example, the annealing temperature is about 2-35° C., 4-35° C., 5-25° C., 6-20° C., 6-15° C. higher than the gene-specific annealing temperature in step (f). In step (g), the PCR cycling is repeated at least 2 times, e.g., 2-50 times, preferably 2-5, 5-10, 10-30, 10-40, or 10-50 times.

Any added bases can increase the primer's melting temperature when the primer sequences match the template 100%. In the present invention, the tag sequences are at least 2 or 3 nucleotides in length, and can be 5-100, 3-40, 10-30, 10-40, 10-50 nucleotides long. Preferably, tags are designed to add at least 5° C. (e.g., 5-10° C. or 5-15° C.) to the melting temperature of the gene-specific untagged primers. The tag sequences provide a higher annealing temperature of the cycling conditions after the initial minimal 2 cycles in PCR. Tag sequences can be modified or unmodified nucleic acids. Some modified bases (e.g. LNA or PNA) have higher annealing temperatures than their corresponding natural bases. When shorter tag sequences are desired for various reasons, those modified bases can be used instead of the natural bases.

In one embodiment of the invention, the Tm (melting temperature) of tag t1 sequences on both ends of amplicon 3 is high enough to form a tight t1-stem, which prevents the hybridization of primer t1F2 to the amplicon 3 template, and inhibits a further exponential amplification of amplicon 3. In order to inhibit the binding of primer t1F2 to amplicon 3 template, the Tm of the t1-stem at the end of amplicon 3 should be the same or higher than the Tm of t1F2 oligo alone. The melting and hybridization of t1-stem at the ends of amplicon 3 follow intramolecular kinetics, and are more favorable than those of the regular intermolecular oligo duplex reactions. Therefore, the same two short complimentary oligo sequences (e.g. 2 to 100 nucleotides) have a much higher Tm when they form a stem connected by a non-complimentary loop in one molecule than Tm of the same two complimentary oligo sequences forming a linear duplex. In addition, the Tm of the stem is not only influenced by the stem sequences but also the loop length (corresponding to the overlapping region). In comparison to a small loop size (e.g. 2-200, 5-200, or 10-100 nucleotides), a large loop size (e.g. greater than 500 nucleotides such as 500-1000 or 500-1500 nucleotides) reduces the stem hybridization rates, possibly due to the decreased probabilities of contact between the ends of the larger loop, and resembles the kinetics of regular intermolecular DNA duplex formations.

In one embodiment, the second nucleic acid sequence optionally further comprises a full sequence (F2), or a partial sequence (F2^) consecutively from the 5' end of the second forward primer (F2), in between the second tag (t1) and the first reverse primer (R1). In FIG. 2, this optional embodiment of primer t1F2^R1 is shown. Dependent on the length of F2, in one embodiment, the partial sequence of F2^ is 1-50, 1-20, 1-10, or 1-5 nucleotides shorter than F2. In one embodiment, the partial sequence of F2^ is at least 3, at least 4, or at least 5 nucleotides. For example, the partial sequence of F2^ may be 2-40, 3-40, 4-40, 5-40, 8-40, 8-30, 8-20, 3-35, 4-35, or 5-35 nucleotides. In another embodiment, the partial sequence of F2^ contains 10-50, 10-90, 20-80, 20-90, 30-70, 40-90, or 50-90% of the F2 sequence. In this embodiment, F2 or F2^ is inserted directly between the gene-specific sequence of R1 and its tag sequence t1.

In another embodiment, the third nucleic acid sequence optionally further comprises a full sequence (R1), or a partial sequence (R1^) consecutively from the 5' end of the first reversed primer (R1), in between the first tag (t1) and the second forward primer (F2). Dependent on the length of R1, in one embodiment, the partial sequence of R1^ is 1-50, 1-20, 1-10, or 1-5 nucleotides shorter than R1. In one embodiment, the partial sequence of R1^ is at least 3, at least 4, or at least 5 nucleotides. For example, the partial sequence of R1^ may be 2-40, 3-40, 4-40, 5-40, 8-40, 8-30, 8-20, 3-35, 4-35, or 5-35 nucleotides. In another embodiment, the partial sequence of R1^ contains 10-50, 10-90, 20-80, 20-90, 30-70, 40-90, or 50-90% of the R1 sequence. In this embodiment, R1 or R1^ is inserted directly between the gene-specific sequence of F2 and its tag sequence t1.

As illustrated at the lower part of FIG. 2, after step (g), amplicon 1 (F1+R1), Amplicon 2 (F2+R2), and Amplicon 4_long (F1+R2) are amplified exponentially by PCR, while the amplification of Amplicon 3_overlap (F2+R1) is inhibited. In FIG. 2, adding t1 to the 5'-end of F2 primer and adding t1F2^ at the 5' end of R1 primer result in the same strand of Amplicon 3_overlap (F2+R1) being flanked by the complementary sequences of t1 and F2^ at the two ends of the same strand. Consequently, at the subsequent annealing steps during cycling, the two t1-F2^ complementary sequences in Amplicon_3 form a strong stem that renders the sequences inaccessible for the hybridization of the forward primer (t1-F2), thus preventing Amplicon 3 from serving as a template for further amplification. The proper length of F2^ that enables a strong stem structure may vary depending on the Tm of tag t1. FIG. 2 illustrates the stem loop formation with t1 and F2^, which is a preferred embodiment. In another embodiment, as described above, the Tm of tag t1 sequences on both ends of amplicon 3 are high enough to form a tight t1-stem, and the presence of F2^ is not required.

In another embodiment of the invention, the above amplification products after the first round of PCR as described above are amplified further by a second round of PCR amplification with universal primers that bind to t1 and t2 in the first round. In this embodiment, t3 is required to be the same as t2 during the first round of PCR. The second PCR round comprises the steps of: (h) mixing the amplification products from (g), either treated or untreated, with a first and a second universal PCR primers that bind to t1 and t2 respectively, and an effective amount of reagents necessary for performing a PCR, wherein both universal PCR primers do not comprise sequences complementary to the first and the second target-specific nucleic acid sequences; and (i) cycling the mixture of (h) through denaturing, annealing and primer extension steps of PCR at standard PCR temperatures and conditions known to a person skilled in the art to obtain second amplification products.

In step (i), the PCR cycling is repeated at least 2 times, e.g., 5-50 times, preferably 2-5, 5-10, 10-30, 10-40, or 10-50 times.

During the second round of PCR, the amplifications of the short overlapping Amplicon 3_overlap and the long Amplicon 4_long are further inhibited because their primer binding sites are blocked by the strong stem formation of t1 at both ends of the Amplicon 3_short and t2 at both ends of the Amplicon 4_long. Therefore, the amplifications of the first and the second target nucleic acid amplicons (Amplicons 1 and 2) dominate in the second round of PCR. The final products can be used for different purposes, such as next generation sequencing (NGS).

In the second round of PCR, the product of (g) from the first round of PCR is optionally pre-treated before the step (i), for example, by dilution, single-strand exonuclease digestion, purification, or adaptor ligation.

The following examples further illustrate the present invention. These examples are intended merely to be illustrative of the present invention and are not to be construed as being limiting.

EXAMPLES

Figure 3:
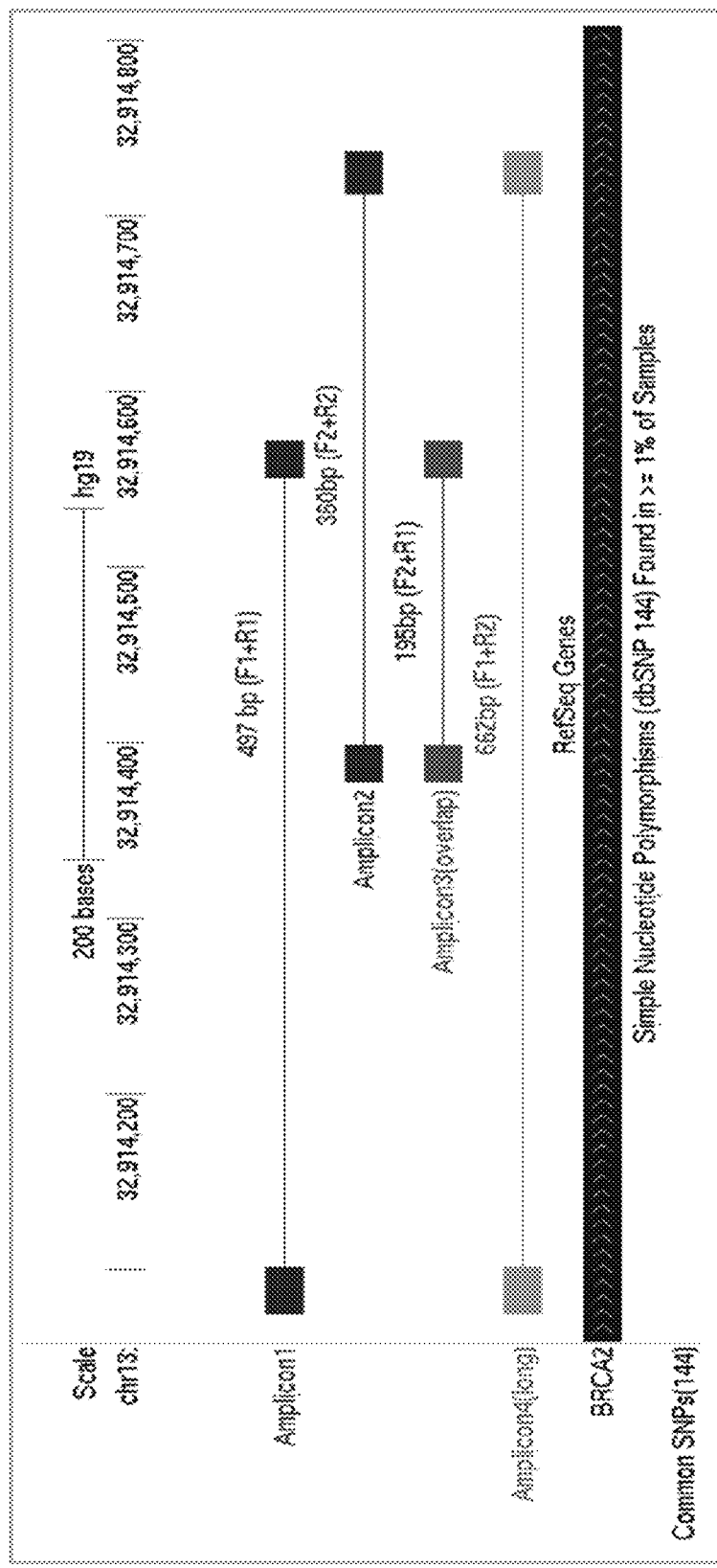
FIG. 3 shows the sizes and locations of Amplicons 1-4 on human chromosome 13 for Examples 1 and 2.

Table 1 and FIG. 3 show the sizes and locations of Amplicons 1-4 on human genome hg19. Amplicon 3 is the overlap between Amplicons 1 and 2. Amplicon 4 is the long amplicon covering the sequences of both Amplicons 1 and 2.

TABLE 1

| Amplicon Name | Gene | Chr. hg19 | Start hg19 | End hg19 | Size Gene-Specific (bp) | Size With Tag (bp) |
|---|---|---|---|---|---|---|
| Amplicon1 | BRCA2 | chr13 | 32914076 | 32914572 | 497 | 538 |
| Amplicon2 | BRCA2 | chr13 | 32914378 | 32914737 | 360 | 401 |
| Amplicon3_overlap | BRCA2 | chr13 | 32914378 | 32914572 | 195 | 236 |
| Amplicon4_long | BRCA2 | chr13 | 32914076 | 32914737 | 662 | 703 |

Figure 4:
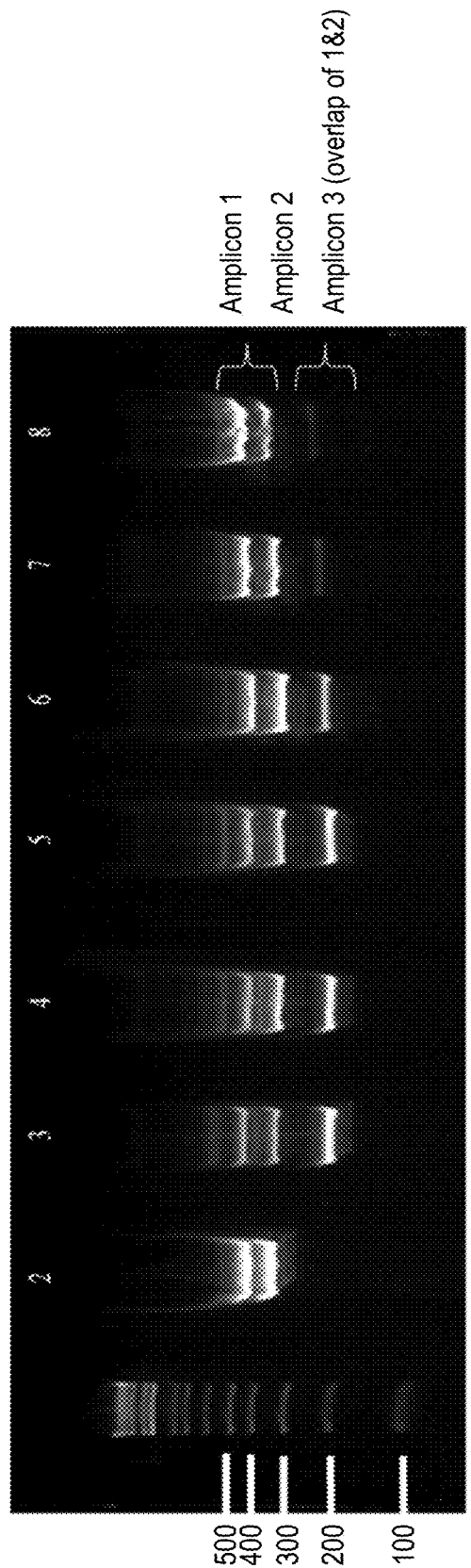
FIG. 4 shows the agarose gel electrophoresis results of the amplification products after the first round of PCR (Examples 1 and 2).

Table 2 shows oligonucleotide sequences used in Examples 1 and 2, and FIG. 4 SEQ ID NOs: 1-4 are gene specific primers for BRCA2 amplicon 1 and amplicon 2 without tag sequences. SEQ ID NOs: 5-6 are tag sequences from Illumina TSCA tags. SEQ ID NOs: 7-16 are the tagged primers used in the example experiments.

SEQ ID NO: 7 was used in standard multiplex PCR only (FIG. 4, Lane 3). SEQ ID NOs: 8-14 were used in the present invention (Lane 4-8). SEQ ID NOs: 15-16 were used in both the standard multiplex PCR and the present invention (Lane 3-8).

Tm are evaluated by OligoAnalyzer 3.1 (IDTDNA) with 1.5 mM of $Mg^{+2}$ concentration.

TABLE 2

| Oligo SEQ ID NO: | | Sequence* | Direction Size (nt) | Amplicon | Gene Specific Oligo-Tm | Tagged Full OligoTm | Stem_Tm_ formed between t1_F2^_R1 and t1_F2, or between t1_R1 and t1_R1^_F2 |
|---|---|---|---|---|---|---|---|
| 1: | F1 | GTGAAAGACATATTTACAGACAGTTTC | FWD 27 | Amplicon1 | 60.6 | N/A | N/A |
| 2: | R1 | CTTGTGAGCTGGTCTGAATGT | REV 21 | Amplicon1 | 61.9 | N/A | N/A |
| 3: | F2 | AGGGAAGCTTCATAAGTCAGTC | FWD 22 | Amplicon2 | 61.3 | N/A | N/A |
| 4: | R2 | TCCTCTAACACTCCCTTAACTTTGT | REV 25 | Amplicon2 | 63.1 | N/A | N/A |
| 5: | t1 | caacgatcgtcgaaattcgc | 20 | Tag | 61.3_TagOnly | N/A | N/A |
| 6: | t2 | tacacgacgctcttccgatct | 21 | Tag | 64.4_TagOnly | N/A | N/A |
| 7: | t1_F1 | caacgatcgtcgaaattcgc GTGAAAGACATATTTACAGACAGTTTC | FWD 47 | Amplicon1 | 60.6 | 72.6 | N/A |
| 8: | t2_F1 | tacacgacgctcttccgatct GTGAAAGACATATTTACAGACAGTTTC | FWD 48 | Amplicon1 | 60.6 | 73.2 | N/A |
| 9: | t2_R1 | tacacgacgctcttccgatct CTTGTGAGCTGGTCTGAATGT | REV 42 | Amplicon1 | 61.9 | 75.2 | N/A |
| 10: t1_R1 (F2^ = 0) | | caacgatcgtcgaaattcgc CTTGTGAGCTGGTCTGAATGT | REV 41 | Amplicon1 | 61.9 | 74.7 | 63.3 |
| 11: t1_F2^4_R1 | | caacgatcgtcgaaattcgc AGGG CTTGTGAGCTGGTCTGAATGT | REV 45 | Amplicon1 | 61.9 | 76.5 | 75.2 |
| 12: t1_F2^8_R1 | | caacgatcgtcgaaattcgc AGGGAAGC CTTGTGAGCTGGTCTGAATGT | REV 49 | Amplicon1 | 61.9 | 77.2 | 77.2 |
| 13: t1_F2^12_R1 | | caacgatcgtcgaaattcgc AGGGAAGCTTCA CTTGTGAGCTGGTCTGAATGT | REV 53 | Amplicon1 | 61.9 | 77.2 | 77.8 |

TABLE 2-continued

| Oligo SEQ ID NO: | Sequence* | Direction Size (nt) | Amplicon | Gene Specific Oligo-Tm | Tagged Full OligoTm | Stem_Tm_ formed between t1_F2^_R1 and t1_F2, or between t1_R1 and t1_R1^_F2 |
|---|---|---|---|---|---|---|
| 14: t1 F2^16_R1 | caacgatcgtcgaaattcgc <u>AGGGAAGCTTCATAAG</u> CTTGTGAGCTGGTCTGAATGT | REV 57 | Amplicon1 | 61.9 | 77.3 | 77.5 |
| 15: t1_F2 (R1^ = 0) | caacgatcgtcgaaattcgc AGGGAAGCTTCATAAGTCAGTC | FWD 42 | Amplicon2 | 61.3 | 73.4 | N/A |
| 16: t2_R2 | tacacgacgctcttccgatct TCCTCTAACACTCCCTTAACTTTGT | REV 46 | Amplicon2 | 63.1 | 74.5 | N/A |
| 26: t1_ R1^8_F2 | caacgatcgtcgaaattcgc <u>CTTGTGAG</u> AGGGAAGCTTCATAAGTCAGTC | FWD 50 | Amplicon2 | 61.3 | 67.7 | 69.1 |
| 27: t1_ R1^12_F2 | caacgatcgtcgaaattcgc <u>CTTGTGAGCTGG</u> AGGGAAGCTTCATAAGTCAGTC | FWD 54 | Amplicon2 | 61.3 | 69.3 | 72.2 |

*Lower case indicates tag sequences; Underline indicates inserted partial F2 sequences (F2^), or inserted partial R1 sequences (R1^); un-labeled upper case sequences are gene-specific sequences. N/A: Not applicable. FWD: forward. REV: reverse Table 3 shows primer mix information in Examples 1 and 2.

TABLE 3

| Lane | Name | Multiplex Primer Mix Amplicon1 | | Amplicon2 | | F2_R1 Short Amplicon Loop Length (nt); Stem Oligo; Stem length (nt) |
|---|---|---|---|---|---|---|
| 1 | M: 100bp Ladder | | | | | |
| 2 | Singleplex Control mix[a] | | | | | Not applicable |
| 3 | STD_Multiplex_ctrl | t1_F1 | t2_R1 | t1_F2 | t2_R2 | no stem loop |
| 4 | Stem_t1-F2^0 | t2_F1 | t1_R1 | t1_F2 | t2_R2 | 195; t1_only; 20 |
| 5 | Stem_t1-F2^4 | t2_F1 | t1_F2^4_R1 | t1_F2 | t2_R2 | 195; t1 + 4 nt of F2; 24 |
| 6 | Stem_t1-F2^8 | t2_F1 | t1_F2^8_R1 | t1_F2 | t2_R2 | 195; t1 + 8 nt of F2; 28 |
| 7 | Stem_t1-F2^12 | t2_F1 | t1_F2^12_R1 | t1_F2 | t2_R2 | 195; t1 + 12 nt of F2; 32 |
| 8 | Stem_t1-F2^16 | t2_F1 | t1_F2^16_R1 | t1_F2 | t2_R2 | 195; t1 + 16 nt of F2; 36 |
| 9[b] | Stem_t1-R1^8 | t1_F1 | t1_R1 | t1_R1^(=8)_F2 | t2_R2 | 195; t1 + 8 nt of R1; 28 |
| 10[b] | Stem_t1-R1^12 | t2_F1 | t1_R1 | t1_R1^(=12)_F2 | t2_R2 | 195; t1 + 12 nt of R1; 3 |

[a] Contains each singleplex product from separate amplifications mixed at the equal volume ratio
[b] Data not shown

Example 1

First Round of PCR Amplification (Gene-Specific Primers)

A representative PCR mixture of 25 μL included the following components: 12.5 μL of 2× Multiplex Master Mix (KAPA Biosystems, Cat #KK5802), 2 μL human genomic DNA (Promega, Cat #G3041) diluted to 5 ng/μL in low TE buffer (USB, Cat #75793), 6.5 μL nuclease-free water, and 4 μL of gene-specific primer mix (1.25 μM each, see Multiplex Primer Mix Lanes 3-8 in Table 3).

The singleplex (FIG. 4, Lane 2) PCR, the standard multiplex (FIG. 4, Lane 3) PCR, and the stem-forming multiplex (FIG. 4, Lanes 4-8) PCR were all performed on a thermal cycler as follows:

| 1 cycle | 95° C. | 2 minutes | Enzyme activation and initial DNA denaturation |
| 5 cycles | 95° C. | 30 seconds | Denaturation |
| | 60° C. | 90 seconds | Annealing/extension |
| 30 cycles | 95° C. | 30 seconds | Denaturation |
| | 72° C. | 90 seconds | Annealing/extension at an increased temperature |
| 1 cycle | 72° C. | 5 minutes | Final extension |
| 1 cycle | 8° C. | Hold | |

Example 2

Agarose Gel Electrophoresis

The products from example 1 were analyzed on an E-base device (Life Technologies). Two μL of the product was diluted to a final volume of 20 μL with nuclease-free water and loaded onto a 2% SizeSelect E-gel. DNA electrophoresis of diluted PCR products (Lanes 2-8) and 1 Kb Plus DNA ladder (Invitrogen, Cat #10488-090, Lane 1) was performed, and at the end of the run, a digital image of the gel was captured by an E-gel Imager (Life Technologies). Results are shown in FIG. 4.

In Lane 2 of FIG. 4, equal amounts of the products of singleplex reactions from Example 1 are mixed and can be seen together on the gel, designated Amplicons 1 and 2. Standard multiplex PCR predominantly produces Amplicon 3 (Lane 3), which is PCR product amplified from the overlap of Amplicons 1 and 2. Amplicon 4, the entire region covered by Amplicons 1 and 2, can faintly be seen in Lane 3. Lanes 4 and 5, which contain stem oligonucleotides of t1 only and t1 plus partial F2 (4 nucleotides from the 5' end), respectively, show similar patterns with three detectable bands: Amplicons 1, 2 and 3. In Lanes 6-8, all Amplicons 1, 2, and 3 can be seen, but amplicon 3 has decreased substantially relative to Lanes 3-5.

Figure 5:
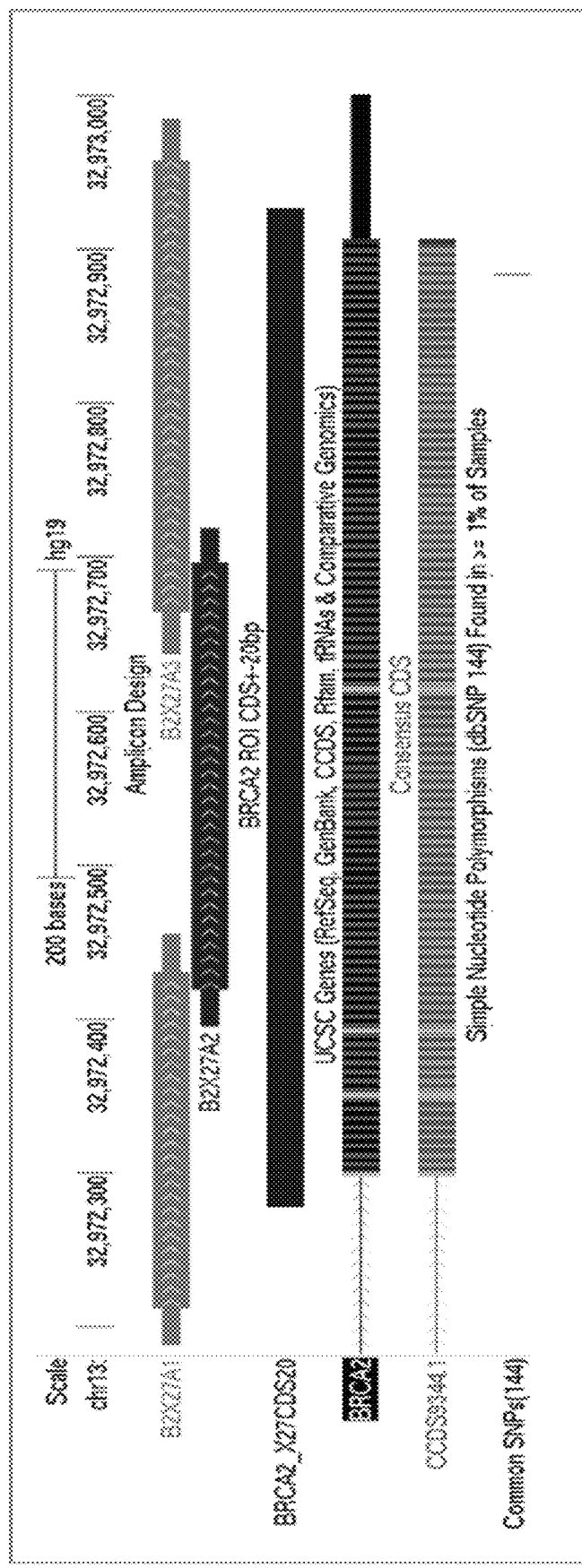
FIG. 5 is a schematic illustration of the gene-specific amplicons used in examples 3-6. CDS: protein coding sequence region of a gene; ROI: region of interest. In this example, ROI includes the CDS of BRCA2 gene exon 27 plus 20 bp upstream and 20 bp downstream of exon 27 (CDS±20 bp).

Table 4 and FIG. 5 show the amplicon sizes and locations on human genome hg19 targeting BRCA2 Exon 27 (B2X27) used in examples 3-6.

TABLE 4

| Amplicon Name | chr_hg19 | Start hg19 | End hg19 | Amplicon Size Gene-Specific (bp) | Amplicon Size With Tag (bp) |
|---|---|---|---|---|---|
| B2X27A1 | chr13 | 32972189 | 32972455 | 267 | 308 |
| B2X27A2 | chr13 | 32972396 | 32972719 | 324 | 365 |
| B2X27A3 | chr13 | 32972638 | 32972985 | 348 | 389 |
| Overlap of B2X27A1 + A2 | chr13 | 32972396 | 32972455 | 60 | 101 |
| Overlap of B2X27A2 + A3 | chr13 | 32972638 | 32972719 | 82 | 123 |

Table 5 shows oligonucleotide sequences used in Examples 3, 4, 5, and 6 for BRCA2 (B2) Exon 27 (×27) amplification.

TABLE 5

| Oligo SEQ ID NO: | Sequence* | Direction Size (nt) | Amplicon |
|---|---|---|---|
| 17: t1_B2X27A1F | caacgatcgtcgaaattcgc ACTGTGTGTAATATTTGCGTGCTT | FWD 44 | B2X27A1 |
| 18: t2_B2X27A1R | tacacgacgctcttccgatct TTCTCTTTTTGCAGTTCTTTTGGT | REV 45 | B2X27A1 |
| 19: t1_B2X27A2F | caacgatcgtcgaaattcgc CTTCAAAGTCTTGTAAAGGGGAGA | FWD 44 | B2X27A2 |
| 20: t2_B2X27A2R | tacacgacgctcttccgatct TTGAACCAGACAAAAGAGCTTG | REV 43 | B2X27A2 |
| 21: t1_B2X27A3F | caacgatcgtcgaaattcgc GAAATTTCTCTTTTGGAAAGTAATTCA | FWD 47 | B2X27A3 |
| 22: t2_B2X27A3R | tacacgacgctcttccgatct TGTGGTTTGAAATTATATTCCAGTCTT | REV 48 | B2X27A3 |
| 23: t2_B2X27A1.SLIM.R | tacacgacgctcttccgatct CTTCAAAGTC TTCTCTTTTTGCAGTTCTTTTGGT | REV 55 | B2X27A1 |
| 24: t2_B2X27A2.SLIM.F | tacacgacgctcttccgatct CTTCAAAGTCTTGTAAAGGGGAGA | FWD 45 | B2X27A2 |
| 25: t1_B2X27A2.SLIM.R | caacgatcgtcgaaattcgc GAAATTTCTCT TTGAACCAGACAAAAGAGCTTG | REV 53 | B2X27A2 |

*Lower case indicates tag sequences; Underline indicates inserted partial forward primer sequences from the next amplicon; un-labeled, upper case sequences are gene-specific sequences.

Example 3

First Round of Gene-Specific PCR Amplification for BRCA2 Exon 27 (B2X27)

A representative PCR mixture of 25 µL included the following components: 12.5 µL of 2× Multiplex Master Mix (KAPA Biosystems, Cat #KK5802), 6 uL of DNA (Coriell, Cat #NA19240 or NA14622) diluted to 5 ng/µL in low TE buffer (IDT, Cat #11-05-01-09), 2.5 µL nuclease-free water, and 4 µL of gene-specific primer mix (1.25 µM each).

The conventional primer mix contained the following six oligos from Table 5: SEQ ID NOs: 17 and 18 (B2X27 amplicon 1), 19 and 20 (B2X27 amplicon 2), and 21 and 22 (B2X27 amplicon 3). The SLIMAMP™ primer mix (the present invention) contains the following six oligos: 17 and 23 (B2X27 amplicon 1), 24 and 25 (B2X27 amplicon 2), and 21 and 22 (B2X27 amplicon 3).

The standard multiplex and stem-forming multiplex PCR is performed on a thermal cycler as follows:

| | | | |
|---|---|---|---|
| 1 cycle | 95° C. | 2 minutes | Enzyme activation and initial DNA denaturation |
| 5 cycles | 95° C. | 15 seconds | Denaturation |
| | 60° C. | 6 minutes | Annealing/extension |
| 25 cycles | 95° C. | 30 seconds | Denaturation |
| | 72° C. | 3 minutes | Annealing/extension at increased temperature |
| 1 cycle | 8° C. | Hold | |

Example 4

Second Round of PCR Amplification (Universal Primers) and Purification

The gene-specific products in Example 3 were diluted 1000-fold. A representative PCR mixture of 25 µL included the following components: 2.5 µL 10× reaction buffer, 0.5 µL dNTPs, 0.25 µL enzyme (Roche, Cat #12140314001), 2 µL of the diluted product from Example 3, 2 µL of Illumina Index Forward primer, 2 µL Illumina Index Reverse primer (25 µM primer stock from TruSeq Custom Amplicon Index Kit, Cat #FC-130-1003), and 15.75 µL nuclease-free water.

PCR amplification was performed as follows:

| | | | |
|---|---|---|---|
| 1 cycle | 95° C. | 4 minutes | Initial DNA denaturation |
| | 95° C. | 30 seconds | Denaturation |
| 20 cycles | 66° C. | 30 seconds | Annealing |
| | 72° C. | 60 seconds | Extension |
| 1 cycle | 72° C. | 5 minutes | Final extension |
| 1 cycle | 8° C. | Hold | |

The product was purified by adding 18 µL of Agencourt AMPure XP beads (Beckman Coulter, Cat #A63881), separating the beads from the supernatant, and discarding the supernatant. Two washes of 70% ethanol were used to wash the beads, and the product was eluted from the beads using 32 µL nuclease-free water. The concentration of the product was then quantified using 2 µL of the product diluted in 198 µL of Qubit High Sensitivity buffer (Invitrogen, Cat #Q32854).

Example 5

Agarose Gel Electrophoresis

The products from example 3 and example 4 were analyzed on an E-base device (Life Technologies). Two µL of the product was diluted to a final volume of 20 µL with nuclease-free water and loaded onto a 2% SizeSelect E-gel. DNA electrophoresis of diluted PCR products and 50 bp DNA ladder (Invitrogen, Cat #10488-043) was performed. At the end of the run, a digital image of the gel was captured by an E-gel Image (Life Technologies). Results are shown in FIG. 6.

Figure 6:
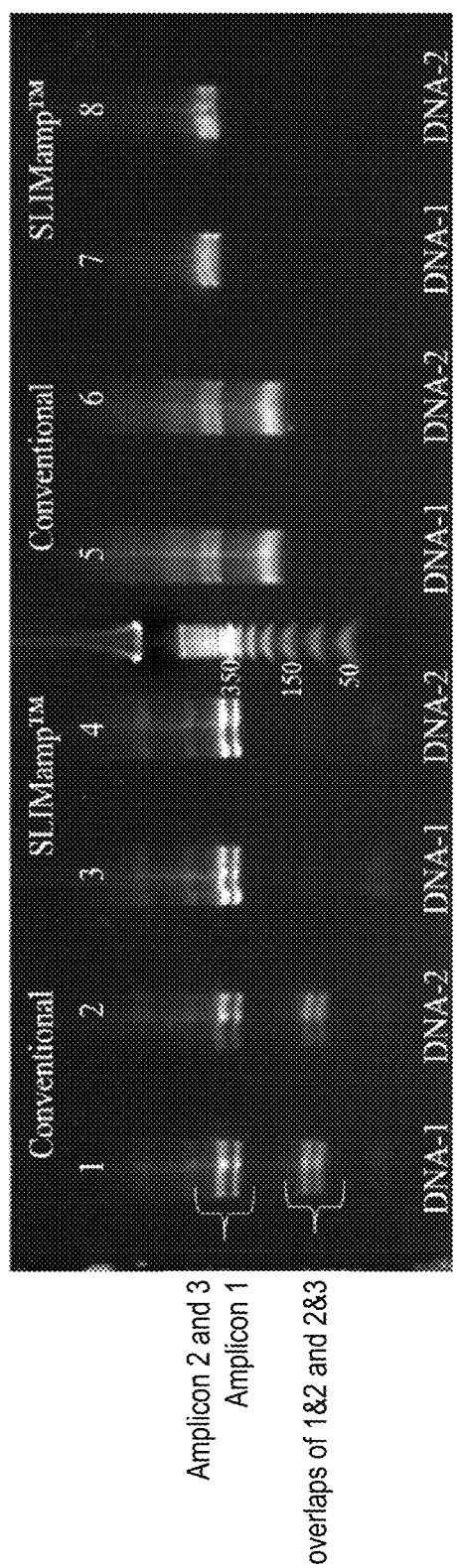
FIG. 6 shows the agarose gel electrophoresis results of amplification products after the first round (Example 3) and second round of PCR (Example 4).

The products from example 3 (First round of PCR products) are shown in Lane 1-4 of FIG. 6. Lanes 1 and 2 demonstrate the products of conventional multiplex PCR. The small amplicons, which are the overlaps of amplicons 1 with 2 and 2 with 3, were produced along with amplicons 1-3. On the other hand, SLIMAMP™ reactions, loaded in Lanes 3 and 4, produce mainly amplicons 1-3, with very little of the overlapping amplicons.

The products from Example 4 (second round of PCR products) are shown in Lanes 5-8 of FIG. 6, which are products after universal PCR and cleaned up by beads. In Example 4 (Lanes 5-8), amplicons were tagged and amplified further, demonstrated by the increase in nucleotide size when compared with Lanes 1-4. The samples that originally underwent conventional multiplex PCR produced primarily the undesired short overlapping amplicons (Lanes 5-6), while the SLIMAMP™ samples (the present invention) contain only the targeted amplicons 1-3 (Lanes 7-8).

Example 6

NGS Library Normalization and Sequencing

Each product from Example 4 was normalized to 4 mM using 10 mM Tris-HCl w/0.1% Tween 20 (Teknova, Cat #T7724). All normalized products from Example 4 are mixed in equal volume (3 µL each) to create a library mix. 5 µL of the library mix is added to 5 µL of 0.2 N NaOH to denature the library. A 20 pM library is prepared using HT1 buffer, loaded, and sequenced with a 250 bp paired-end read length (Illumina, Cat #MS-102-2003). The resulting Fastq sequencing reads for each sample was then aligned to the hg19 reference genome by BWA-MEM. The paired-end reads were then merged and the coverages for each amplicon regions were analyzed. The coverage information is shown in FIG. 7.

Figure 7:
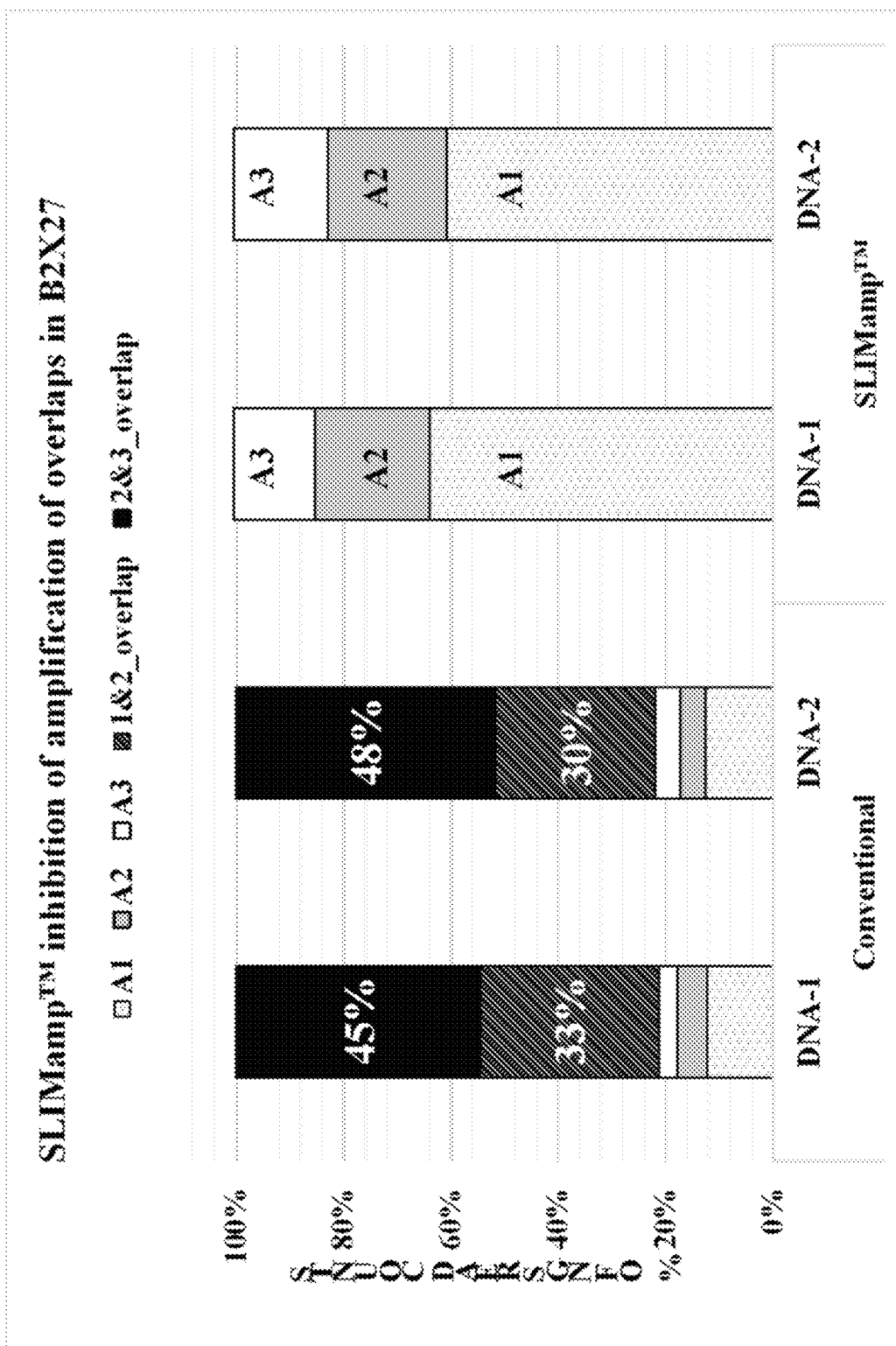
FIG. 7 is a chart showing the coverage data from NGS results of amplicons (Example 6).

FIG. 7 depicts the percentage of NGS reads attributed to each amplicon in each sample. In the conventional multiplex PCR, the overlapping amplicons were amplified more efficiently than the target amplicons and count for 78% of the total NGS reads, due to their much smaller sizes (60 and 82 bp). In the SLIMAMP™ samples, all the undesired overlapping amplicons were inhibited with close to 0% detected in NGS. With respect to the targeted amplicons in both the conventional and SLIMAMP™ samples, as expected, amplicon 1 (267 bp) had higher percentage than both amplicons 2 (324 bp) and 3 (348 bp) because a smaller size (amplicon 1) typically amplifies more efficiently.

It is to be understood that the foregoing describes preferred embodiments of the present invention and that modifications may be made therein without departing from the scope of the present invention as set forth in the claims.

What is claimed is:

1. A method for selectively amplifying target nucleic acid fragments having an overlapping region, comprising the steps of:
   (a) obtaining a first nucleic acid sequence comprising a first tag (t2) and a first forward primer (F1) complementary to a first target nucleic acid fragment,
   (b) obtaining a second nucleic acid sequence comprising a second tag (t1) and a first reverse primer (R1) complementary to the first target nucleic acid fragment,
   (c) obtaining a third nucleic acid sequence comprising the second tag (t1) and a second forward primer (F2) complementary to a second target nucleic acid fragment,
   (d) obtaining a fourth nucleic acid sequence comprising a third tag (t3), and a second reverse primer (R2) complementary to the second nucleic acid fragment, wherein the first and the second target nucleic acid fragments have an overlapping region,
   (e) mixing the first and the second target nucleic acid fragments, the first, the second, the third, and the fourth nucleic acid sequences, and an effective amount of reagents necessary for performing a polymerase chain reaction (PCR);
   (f) cycling the mixture of (e) through denaturing, annealing and primer extension steps of PCR for at least two times, and
   (g) cycling the mixture of (f) through denaturing, annealing and primer extension steps of PCR at an annealing temperature 5-25° C. higher than that in step (f) to obtain amplification products,
   wherein the second nucleic acid sequence further comprises a full sequence of the second forward primer (F2), in between the second tag (t1) and the first reverse primer (R1).

2. A method for selectively amplifying target nucleic acid fragments having an overlapping region, comprising the steps of:
   (a) obtaining a first nucleic acid sequence comprising a first tag (t2) and a first forward primer (F1) complementary to a first target nucleic acid fragment,
   (b) obtaining a second nucleic acid sequence comprising a second tag (t1) and a first reverse primer (R1) complementary to the first target nucleic acid fragment,
   (c) obtaining a third nucleic acid sequence comprising the second tag (t1) and a second forward primer (F2) complementary to a second target nucleic acid fragment,
   (d) obtaining a fourth nucleic acid sequence comprising a third tag (t3), and a second reverse primer (R2) complementary to the second nucleic acid fragment, wherein the first and the second target nucleic acid fragments have an overlapping region,
   (e) mixing the first and the second target nucleic acid fragments, the first, the second, the third, and the fourth nucleic acid sequences, and an effective amount of reagents necessary for performing a polymerase chain reaction (PCR),
   (f) cycling the mixture of (e) through denaturing, annealing and primer extension steps of PCR for at least two times, and
   (g) cycling the mixture of (f) through denaturing, annealing and primer extension steps of PCR at an annealing temperature 5-25° C. higher than that in step (f) to obtain amplification products, wherein the second nucleic acid sequence further comprises F2ˆ, which is a 5'-end partial sequence of the second forward primer (F2), in between the second tag (t1) and the first reverse primer (R1).

3. The method according to claim 2, wherein F2ˆ contains 10-90% of the F2 sequence.

4. The method of claim 2, wherein F2ˆ contains 2-40 nucleotides.

5. The method of claim 2, wherein F2ˆ contains 4-40 nucleotides.

6. The method of claim 2, wherein F2ˆ is 1-5 nucleotides shorter than F2.

7. A method for selectively amplifying target nucleic acid fragments having an overlapping region, comprising the steps of:
   (a) obtaining a first nucleic acid sequence comprising a first tag (t2) and a first forward primer (F1) complementary to a first target nucleic acid fragment,
   (b) obtaining a second nucleic acid sequence comprising a second tag (t1) and a first reverse primer (R1) complementary to the first target nucleic acid fragment,
   (c) obtaining a third nucleic acid sequence comprising the second tag (t1) and a second forward primer (F2) complementary to a second target nucleic acid fragment,
   (d) obtaining a fourth nucleic acid sequence comprising a third tag (t3), and a second reverse primer (R2) complementary to the second nucleic acid fragment, wherein the first and the second target nucleic acid fragments have an overlapping region,
   (e) mixing the first and the second target nucleic acid fragments, the first, the second, the third, and the fourth nucleic acid sequences, and an effective amount of reagents necessary for performing a polymerase chain reaction (PCR),
   (f) cycling the mixture of (e) through denaturing, annealing and primer extension steps of PCR for at least two times, and
   (g) cycling the mixture of (f) through denaturing, annealing and primer extension steps of PCR at an annealing temperature 5-25° C. higher than that in step (f) to obtain amplification products, wherein the third nucleic acid sequence further comprises a full sequence of the first reverse primer (R1), in between the first second tag (t1) and the second forward primer (F2).

8. A method for selectively amplifying target nucleic acid fragments having an overlapping region, comprising the steps of:
- (a) obtaining a first nucleic acid sequence comprising a first tag (t2) and a first forward primer (F1) complementary to a first target nucleic acid fragment,
- (b) obtaining a second nucleic acid sequence comprising a second tag (t1) and a first reverse primer (R1) complementary to the first target nucleic acid fragment,
- (c) obtaining a third nucleic acid sequence comprising the second tag (t1) and a second forward primer (F2) complementary to a second target nucleic acid fragment,
- (d) obtaining a fourth nucleic acid sequence comprising a third tag (t3), and a second reverse primer (R2) complementary to the second nucleic acid fragment, wherein the first and the second target nucleic acid fragments have an overlapping region,
- (e) mixing the first and the second target nucleic acid fragments, the first, the second, the third, and the fourth nucleic acid sequences, and an effective amount of reagents necessary for performing a polymerase chain reaction (PCR),
- (f) cycling the mixture of (e) through denaturing, annealing and primer extension steps of PCR for at least two times, and
- (g) cycling the mixture of (f) through denaturing, annealing and primer extension steps of PCR at an annealing temperature 5-25° C. higher than that in step (f) to obtain amplification products, wherein the third nucleic acid sequence further comprises a 5'-end partial sequence of the first reverse primer (R1"), in between the first second tag (t1) and the second forward primer (F2).

9. The method according to claim 8, wherein R1^ contains 10-90% of the R1 sequence.

10. The method of claim 8, wherein R1^ contains 2-40 nucleotides.

11. The method of claim 8, wherein R1^ contains 4-40 nucleotides.

12. The method of claim 8, wherein R1^ is 1-5 nucleotides shorter than R1.

13. The method according to claim 2, wherein the PCR cycling in step (f) is repeated 2-10 times.

14. The method according to claim 13, further comprising the steps of:
- (h) mixing the amplification products from step (g), either treated or untreated, with first universal PCR primers and second universal PCR primers that bind to t1 and t2 respectively, but do not bind to the first and the second target nucleic acid fragments, and an effective amount of reagents necessary for performing a PCR, and
- (i) cycling the mixture of step (h) through denaturing, annealing and primer extension steps of PCR to obtain second amplification products.

15. The method of claim 14, wherein the products from step (g) are pre-treated by dilution, single-strand exonuclease digestion, purification, or adaptor ligation.

16. The method according to claim 1, wherein the third tag is the same as the second tag.

* * * * *